(12) United States Patent
Bharate et al.

(10) Patent No.: US 12,036,214 B2
(45) Date of Patent: Jul. 16, 2024

(54) SOLID DISPERSION COMPRISING AN ANTICANCER COMPOUND FOR IMPROVED SOLUBILITY AND EFFICACY

(71) Applicant: COUNCIL OF SCIENTIFIC AND INDUSTRIAL RESEARCH, New Delhi (IN)

(72) Inventors: Sonali Sandip Bharate, Jammu (IN); Vikas Kumar, Jammu (IN); Mubashir Javed Mintoo, Jammu (IN); Dilip Manikrao Mondhe, Jammu (IN); Sandip Bibishan Bharate, Jammu (IN); Ram Vishwakarma, Jammu (IN)

(73) Assignee: COUNCIL OF SCIENTIFIC AND INDUSTRIAL RESEARCH [IN/IN], New Delhi (IN)

( * ) Notice: Subject to any disclaimer, the term of this patent is extended or adjusted under 35 U.S.C. 154(b) by 825 days.

(21) Appl. No.: 17/253,193

(22) PCT Filed: Jun. 14, 2019

(86) PCT No.: PCT/IN2019/050454
§ 371 (c)(1),
(2) Date: Dec. 17, 2020

(87) PCT Pub. No.: WO2020/012498
PCT Pub. Date: Jan. 16, 2020

(65) Prior Publication Data
US 2021/0308116 A1    Oct. 7, 2021

(30) Foreign Application Priority Data
Jul. 13, 2018   (IN) .............................. 201811026240

(51) Int. Cl.
| | |
|---|---|
| A61K 31/453 | (2006.01) |
| A61K 9/10 | (2006.01) |
| A61K 9/20 | (2006.01) |
| A61K 47/10 | (2017.01) |
| A61K 47/32 | (2006.01) |
| A61K 47/38 | (2006.01) |
| A61K 47/40 | (2006.01) |
| A61P 35/00 | (2006.01) |
| C07D 405/04 | (2006.01) |

(52) U.S. Cl.
CPC .............. *A61K 31/453* (2013.01); *A61K 9/10* (2013.01); *A61K 9/2013* (2013.01); *A61K 9/2027* (2013.01); *A61K 9/2054* (2013.01); *A61K 47/10* (2013.01); *A61K 47/32* (2013.01); *A61K 47/38* (2013.01); *A61K 47/40* (2013.01); *A61P 35/00* (2018.01)

(58) Field of Classification Search
CPC ...... A61K 31/453; A61K 9/10; A61K 9/2013; A61K 9/2027; A61K 9/2054; A61K 9/2031; A61K 9/205; A61K 47/10; A61K 47/38; A61K 47/40; A61P 35/00
See application file for complete search history.

(56) References Cited

U.S. PATENT DOCUMENTS

| | | | |
|---|---|---|---|
| 9,932,327 B2 * | 4/2018 | Vishwakarma | C07D 405/04 |
| 2009/0311325 A1 | 12/2009 | Janssens et al. | |
| 2013/0045251 A1 | 2/2013 | Cen et al. | |
| 2016/0052915 A1 | 2/2016 | Vishwakarma et al. | |

FOREIGN PATENT DOCUMENTS

| | | |
|---|---|---|
| CA | 2908084 A1 | 10/2014 |
| EP | 2986605 A1 | 2/2016 |
| WO | WO-2005/020994 A1 | 3/2005 |
| WO | WO-2006/049433 A1 | 5/2006 |
| WO | WO-2006/083130 A1 | 8/2006 |
| WO | WO-2014-170914 | 10/2014 |
| WO | WO 2016/145138 A1 | 9/2016 |
| WO | WO 2018/013693 A1 | 1/2018 |

OTHER PUBLICATIONS

Blagden N et al., "Crystal engineering of active pharmaceutical ingredients to improve solubility and dissolution rates", ScienceDirect, Advanced Drug Delivery Reviews, 2007, 59, pp. 617-630, Elsevier.
Brough C et al., "Amorphous Solid Dispersions and Nano-crystal Technologies for Poorly Water-soluble Drug Delivery", International Journal of Pharmaceutics., 2013, pp. 157-166, vol. 453, http://dx.doi.org/10.1016/j.ijpharm.2013.05.061.
Cao Y et al., "Amorphous Solid Dispersion of Epigallocatechin Gallate for Enhanced Physical Stability and Controlled Release", Pharmaceuticals, 2017, 10, 88.
Lima A et al., "The Use of Solid Dispersion Systems in Hydrophilic Carriers to Increase Benznidazole Solubility", Journal of Pharmaceutical Sciences, vol. 100, No. 6, May 2011; pp. 2443-2451.
Ellenberger D et al., "Expanding the Application and Formulation Space of Amorphous Solid Dispersions with KinetiSol®: a Review", AAPS PharmSciTech, 2018, American Association of Pharmaceutical Scientists.
Halder S et al., "Amorphous solid dispersions of carvedilol along with pH-modifiers improved pharmacokinetic properties under hypochlorhydoria", Department of Pharmacokinetics and Pharmacodynamics, School of Pharmaceutical Sciences, University of Shizuoka, Japan.
Huang Y et al., "Fundamental aspects of solid dispersion technology for poorly soluble drugs", Acta Pharmaceutica Sinica B, 2014, 4(1), pp. 18-25.

(Continued)

*Primary Examiner* — Sun Jae Yoo
(74) *Attorney, Agent, or Firm* — NIXON PEABODY LLP; Jeffrey L. Costellia

(57) ABSTRACT

The present invention is related to the novel solid dispersion formulations of an anticancer compound of formula A and a process for preparing the same wherein the anticancer compound is formulated with hydrophilic polymer. The said formulation showed enhanced dissolution of the anticancer compound and improved in-vivo anticancer activity. The said formulations are useful for the treatment of various types of cancer.

12 Claims, 4 Drawing Sheets

(56) References Cited

OTHER PUBLICATIONS

Mallick S et al., "Current Perspectives of Solubilization: Potential for Improved Bioavailability", Drug Development and Industrial Pharmacy; 2007, vol. 33, pp. 865-873.
Ogawa N et al., "Improvement in the water solubility of drugs with a solid dispersion system by spray drying and hot-melt extrusion with using the amphiphilic polyvinyl caprolactam-polyvinyl acetate-polyethylene glycol graft copolymer and d-mannitol", European Journal of Pharmaceutical Sciences, 2018, vol. 111, pp. 205-214, doi:10.1016/j.ejps.2017.09.014.
Ellenberger D et al., "Improved Vemurafenib Dissolution and Pharmacokinetics as an Amorphous Solid Dispersion Produced by KinetiSol® Processing" AAPS PharmSciTech., American Association of Pharmaceutical Scientists, 2018; PMID:29541940.
Zografi G et al., "Introduction to Amorphous Solid Dispersions", Pharmaceutical Amorphous Solid Dispersions, First Edition, 2015, pp. 1-41, John Wiley & Sons, Inc.
Semjonov K. et al., "The formation and physical stability of two-phase solid dispersion systems of indomethacin in supercooled molten mixtures with different matrix formers", (2016), https://doi.org/10.1016/j.ejps.2016.11.019, European Journal of Pharmaceutical Sciences, 2017, 97, pp. 237-246.
Sharma A. et al., "Preparation and characterization of solid dispersions of carvedilol with PVP K30", Research in Pharmaceutical Sciences, Apr. 2010, vol. 5(1), pp. 49-56.
Sim T. et al., "Characterization and pharmacokinetic study of itraconazole solid dispersions prepared by solvent-controlled precipitation and spray-dry methods", Journal of Pharmacy and Pharmacology, 2017, 69 pp. 1707-1715, Royal Pharmaceutical Society.
Szafraniec J. et al., "Enhanced Dissolution of Solid Dispersions Containing Bicalutamide Subjected to Mechanical Stress", International Journal of Pharmaceutics (2018), May 2018, vol. 542, pp. 18-26, doi: https://doi.org/10.1016/j.ijpharm.2018.02.040.
Vasconcelos T., et al., "Amorphous solid dispersions: Rational selection of a manufacturing process", Advanced Drug Delivery Reviews, 2016; 100, 85.
European Search Report (Application No. 19 833 947.5) mailed Mar. 4, 2022, (4 pgs).
V. Kumar et al., "Binary and Ternary Solid Dispersions of an Anticancer Preclinical lead, IIIM-290: In Vitro and in Vivo Studies", International Journal of Pharmaceutics, Elsevier, NL, vol. 570, 1186839, Sep. 2019 (Sep. 9, 2019), (14pgs).
International Search Report for PCT/IN2019/050454, mailed Sep. 13, 2019.
Written Opinion for PCT/IN2019/05454, mailed Sep. 13, 2019.
Bharate et al., "Discovery and Preclinical Development of IIIM-290, an Orally Active Potent Cyclin-Dependent Kinase Inhibitor", Journal of Medicinal Chemistry, 2018, vol. 61, pp. 1664-1687.
Jaskirat, et al., "Solubility Enhancement by Solid Dispersion Method", A Review, Journal of Drug Delivery & Therapeutics, 2013, vol. 3, Issue. 5, Sep. 1, 2013, pp. 148-155.

* cited by examiner

| Parameter | IIIM-290 | SD formulation | Fold-increase |
|---|---|---|---|
| $C_{max}$ (ng/ml) | 656 | 2150 | 3.27 |
| $AUC_{last}$ | 2570 | 4880 | 1.90 |
| $T_{1/2}$ (h) | 1.92 | 2.97 | 1.55 |
| $MRT_{last}$ (h) | 3.52 | 3.01 | NA |

(a)  (b)

SOLID DISPERSION COMPRISING AN ANTICANCER COMPOUND FOR IMPROVED SOLUBILITY AND EFFICACY

FIELD OF THE INVENTION

The present invention describes the 'solid dispersions' of a poorly soluble anti-cancer compound (1'R,2'S)-2-(2,6-dichlorostyryl)-5,7-dihydroxy-8-(3-hydroxy-1-methylpiperidin-4-yl)-4H-chromen-4-one of Formula A with improved efficacy. The solid dispersion of Formula A displayed improved aqueous solubility, in-vitro dissolution rate, oral pharmacokinetics and improved in-vivo anticancer activity over the compound of Formula A. The process of preparing the said dispersion comprises the blending or dispersing the compound of Formula A in pharmaceutically acceptable hydrophilic carriers/polymers/surfactants using solvent evaporation method.

BACKGROUND OF THE INVENTION

Oral route is most suitable and widely used for the administration of drugs. The oral bioavailability of a drug is mostly dependent on its solubility, dissolution and absorption in the gastrointestinal tract (GIT). The oral bioavailability and efficacy of poorly water soluble drugs is compromised because of limited solubility and dissolution in the GIT. There are large numbers of highly potent bioactive compounds available in literature, however with poor water solubility. For such lipophilic candidates, numerous solubility enhancing approaches exist including crystal engineering, solid dispersions, size reduction (micronization, nanosuspensions and nanoparticles), amorphous transformation, self emulsifying drug delivery systems, application of various solubilizing and pH modifying agents in formulation (Blagden N. et al., Adv. Drug Deliv. Rev. 2007, 59, 617; Mallick S. et al., Drug Dev Ind Pharm. 2007, 33, 865; Brough C. and Williams R. O., Int. J. Pharm., 2013, 453, 157). In particular, the solid dispersion approach has wide applications among these techniques for solubility and dissolution enhancement because of its easy scale-up from the lab-to-pilot scale and its cost effectiveness compared to other techniques. A number of solid dispersion based formulations are available in the market including Cesamet®, Kaletra®, Zortress®, Incivek™, Noxafil®, Mavyret™ etc (Vasconcelos T., et al., Adv. Drug Deliv. Rev. 2016, 100, 85).

Solid dispersion formulations are compositions in which one or more active pharmaceutical ingredient (API) is dispersed into hydrophilic excipient(s). Excipients used in solid dispersions are generally hydrophilic or amphiphilic polymers or their combination with some cross-linked polymers with low water solubility. The resulting dispersion shows improved solubility/apparent solubility and dissolution profile of the API resulting in an improved bioavailability after oral administration. These polymers improve the wettability of compound in aqueous media, increase the surface area because of the porous nature of formed particles, and stabilize the drug in amorphous form (Zografi G. and Newman A., *Pharmaceutical amorphous solid dispersions*, John Wiley & Sons, 2015, pp. 1). In literature, the technology of solid dispersions has been used successfully to improve the dissolution profile of several poorly soluble drugs. There are numerous reports on the preparation of solid dispersions of drugs or biologically active compounds; from which some of the representative examples include carvedilol (Sharma A and Jain C P, *Res. Pharm. Sci.* 2010, 5, 49-56; Halder S et al, *Biopharm Drug Dispos.* 2018, 39, 232), vemurafenib (Ellenberger D J et al., *AAPS PharmSciTech.* 2018, PMID: 29541940), bicalutamide (Szafraniec J et al., *Int J Pharm.* 2018, 542, 18-26), and itraconazole (Sim T et al., *J Pharm Pharmacol.* 2017, 69, 1707-1715).

Among the patent literature, the PCT application WO2006083130A1 has claimed the amorphous taclolimus (an immunosuppressive drug) solid dispersion (comprising cyclodextrin derivative and organic acid) with high thermodynamic stability, high solubility, enhanced release rate and bioavailability. WO2005020994A1 discloses another solid dispersion of taclolimus with improved bioavailability. US20130045251A1 discloses the solid dispersions of prasugrel (platelet aggregation inhibitor) with improved dissolution rate. WO2006049433A1 discloses the solid dispersion composition of pranlukast (anti-asthma drug) with improved bioavailibility Solid dispersions approach has also been used to improve the physical stability of the drug e.g. epigallocatechin gallate (Cao Y et al., *Pharmaceuticals* (Basel). 2017, 10, pii: E88), indomethacin (Semjonov K et al., *Eur J Pharm Sci.* 2017, 97, 237-246; Ogawa N et al., *Eur J Pharm Sci.* 2018, 111, 205-214). Different hydrophilic polymers which are commonly used for solid dispersion are PVP, HPMC, PVP/VA and HPMCAS (See reviews: Huang Y and Dai W G, *Acta Pharm.* Sin. B, 2014, 4, 18-25; de Lima A A N et al., *Braz. J. Pharm.* 2011, 92, 269-278).

The preclinical candidate of formula A is a semisynthetic derivative of natural product rohitukine, a major constituent of *Dysoxylum binectariferum* (Family: Meliaceae). Compound of formula A possess strong inhibition of Cdk-9/T1 ($IC_{50}$=1.9 nM) kinase and Molt-4/MIAPaCa-2 cell growth ($GI_{50}$<1.0 µM) and was found to be highly selective for cancer cells over normal fibroblast-cells. This is an orally bioavailable compound with in-vivo efficacy in pancreatic, colon and leukemia xenograft models. It did not have CYP/efflux-pump liability, was not mutagenic/genotoxic or cardiotoxic and was metabolically-stable (Bharate S. B. et al., *J. Med. Chem.*, 2018, 61, 1664; U.S. Pat. No. 9,932, 327B2 (US20160052915); WO2014170914A1, EP2986605, CA2908084, IN2013DE01142).

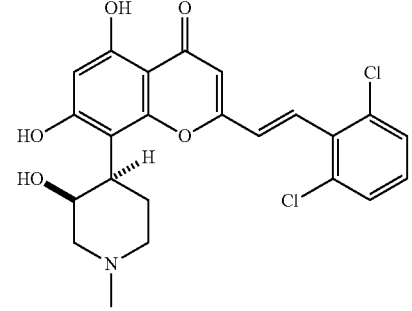

Formula A

Despite of its good oral bioavailability, the poor dissolution property of this compound is a limiting factor for its potent effect in in-vivo models. The in-vivo efficacy of this compound was observed, comparatively at a higher dose, than that of its theoretically required dose. Therefore, an effort towards improvement of its dissolution property was a key requirement to enhance its in-vivo efficacy. The present invention relates to aqueous solubility, dissolution rate, pharmacokinetics and in-vivo anticancer activity improvement of this compound (formula A). The invention describes the preparation of solid dispersions of compound of formula A that results in improved dissolution, improved oral pharmacokinetics and improved oral efficacy in tumor models, compared to the compound of Formula A.

OBJECTIVES OF THE INVENTION

The objective of this invention is to provide, a solid dispersion comprising an anticancer compound (1'R,2'S)-2-(2,6-dichlorostyryl)-5,7-dihydroxy-8-(3-hydroxy-1-methylpiperidin-4-yl)-4H-chromen-4-one of Formula A.

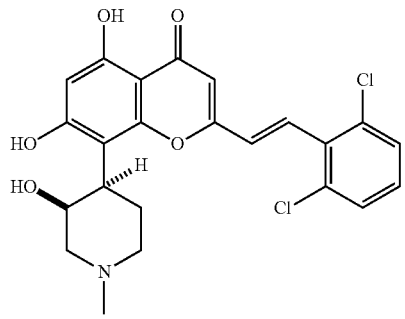

Formula A

Another objective of the invention is to provide the solid dispersion comprising an anticancer compound of Formula A dispersed in a hydrophilic polymer.

Another objective of the invention is to provide, a pharmaceutical composition comprising the solid dispersion.

Another objective of the invention is to provide a method for the preparation of the solid dispersion.

Another objective of the invention is to provide an oral formulation for the oral delivery of an anticancer compound of Formula A.

Another objective of the invention is to enhance the aqueous solubility and thereby the dissolution profile of the compound of Formula A.

Another objective of the invention is to enhance in-vivo efficacy of the compound of Formula A, after its oral administration.

Another objective of the invention is to reduce the effective dose of the compound of Formula A.

SUMMARY OF THE INVENTION

Accordingly, the present invention provides a solid dispersion comprising an anticancer compound (1'R,2'S)-2-(2,6-dichlorostyryl)-5,7-dihydroxy-8-(3-hydroxy-1-methylpiperidin-4-yl)-4H-chromen-4-one of formula A dispersed in a hydrophilic polymer at an ambient temperature, wherein the anticancer compound is present in a concentration range of 15% w/w to 30% w/w of solid dispersion.

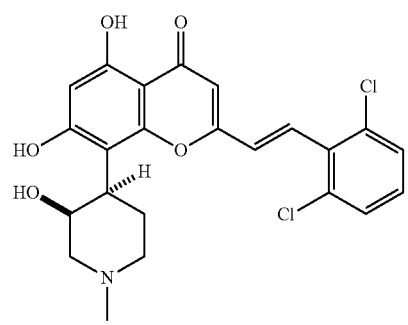

Formula A

In an embodiment of the present invention, the hydrophilic polymer is selected from the group consisting of hydroxypropylcellulose, hydroxypropylmethylcellulose, hydroxypropylmethylcellulose acetate succinate, polyvinylpyrrolidone K12-K120, polyvinyl alcohol, copolyvidone, polyethylene glycol, polyethylene glycol(15)-hydroxystearate, poly(ethylene glycol)-block-poly(propylene glycol)-block-poly(ethylene glycol), 2-hydroxypropyl-beta-cyclodextrin and combination thereof.

In the preferred embodiment of the present invention, the weight ratio of the anticancer compound to the hydrophilic polymer(s) is 1:4.

In another embodiment of the present invention, at least 75% of the anticancer compound is released within about 60 minutes, when tested in any dissolution test according to USP using an aqueous dissolution medium.

In another embodiment of the present invention, the plasma exposure and percent tumor growth inhibition of solid dispersion of Formula A is enhanced at least by 1.5 times in comparison to the compound of formula A.

In another embodiment the present invention provides a pharmaceutical composition comprising the solid dispersion and one or more pharmaceutically acceptable excipients.

In a preferred embodiment of the present invention the pharmaceutically acceptable excipients are selected from the group consisting of fillers, and lubricants.

In a preferred embodiment of the present invention the fillers are selected from the group of microcrystalline cellulose, dicalcium phosphate, sucrose, and lactose.

In a preferred embodiment of the present invention the lubricants are selected from the group consisting of sodium lauryl sulphate, silicon dioxide, magnesium stearate, sodium benzoate, sodium acetate, sodium carboxymethyl cellulose, and boric acid.

In a preferred embodiment of the present invention the composition is in a solid oral dosage form.

In another embodiment the present invention provides a solid dispersion and pharmaceutical composition comprising solid dispersion for use in the treatment of cancer.

In one preferred embodiment of the invention, the orally-administrable composition for the improved dissolution profile of anticancer compound comprises uniformly dispersed anticancer compound in at least one hydrophilic polymer and is characterized by improved in-vitro dissolution profile of compound over a period of 6 hrs, as determined by U.S.P. dissolution apparatus by paddle method at a speed of 50 rpm and temperature 37° C.±0.5 under different dissolution sink conditions.

In one of the embodiment of the invention, at least 75% of the a anticancer compound is released within about 60 minutes in case of the solid dispersion, when tested in any dissolution test according to USP using an aqueous dissolution medium.

In another embodiment the present invention provides a method for the preparation of the solid dispersion comprising the step of dispersing the anticancer compound of formula A in a hydrophilic polymer to obtain a solid dispersion at ambient temperature, wherein the anticancer compound is present at a concentration range of 15% w/w to 30% w/w.

In another preferred embodiment of the invention, the pharmaceutical composition is in the form selected from the group consisting of a tablet or a hard gelatin capsule.

The invention also comprises a process for the preparation of an orally-administrable solid dispersion pharmaceutical composition for the improved solubility and dissolution profile of the anticancer compound. The steps for the preparation of said composition comprising anticancer compound and polyvinylpyrrolidone-K30 (PVP-K30, povidone) are provided below. The solid dispersion pharmaceutical compositions can be prepared by any method including solvent evaporation, fusion method, hot melt extrusion and supercritical fluid method. One exemplary composition using solvent evaporation contains following steps:

a) making a solution of the anticancer compound in organic solvent either in any one or mixture of solvents including methanol, ethanol, isopropyl alcohol, chloroform, dichloromethane, tetrahydrofuran, etc;
b) making a solution of the PVP-K30 in organic solvent either in any one or mixture of solvents including methanol, ethanol, isopropyl alcohol, chloroform, dichloromethane, tetrahydrofuran, etc;
c) mixing the two solutions from step a & b in a desired ratio ranging from 1:1 to 1:10;
d) the solvent from the solution obtained in step (c) was evaporated using either vacuum drying or using spray dryer to obtain a dried product;
e) grinding of dried product obtained in step (d) in moisture-free environment and passing through sieve #30 to obtain the solid dispersion;
f) analysing the obtained solid dispersion for the % content of anticancer compound using HPLC;
g) preparing the solid dispersion pharmaceutical composition in the form of tablet by compressing the solid dispersion obtained in step (e) optionally with a pharmaceutical excipient or in the form of capsules by filling the solid dispersion in hard-gelatin capsules.

In another embodiment, the present invention provides a process for treatment of cancer by administering an effective dose of the solid dispersion.

DETAILED DESCRIPTION OF THE INVENTION

Figure 1:
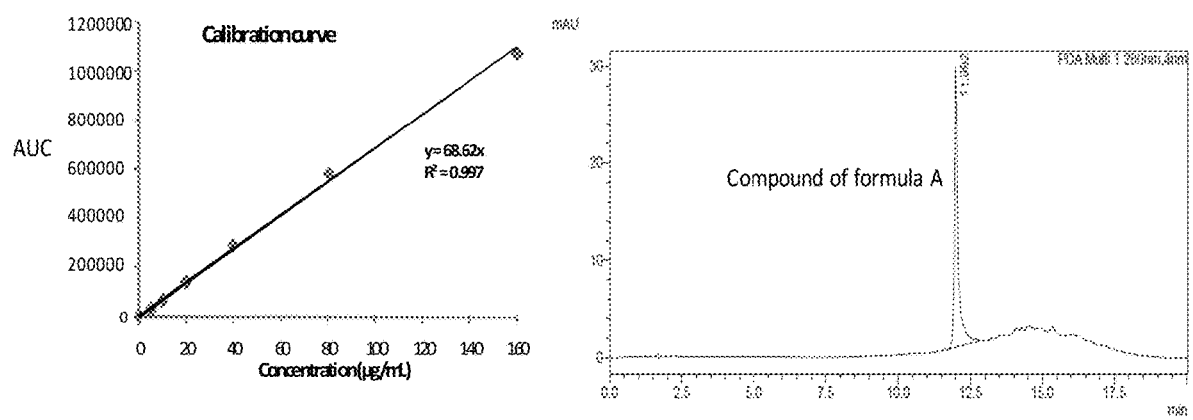
FIG. 1 shows the HPLC chromatograms and calibration curve plot of "compound of formula A". Label of peak indicate the retention time.

The term "composition" and "formulation" are used interchangeably herein.

The term "anticancer compound of formula A", "compound of formula A", "Formula A", "anticancer compound (1'R,2'S)-2-(2,6-dichlorostyryl)-5,7-dihydroxy-8-(3-hydroxy-1-methylpiperidin-4-yl)-4H-chromen-4-one of Formula A", "plain compound" are used interchangeably herein.

The present invention provides the novel solid dispersion of anticancer compound of formula A with improved oral efficacy for the treatment of various types of cancers. More specifically, the invention is directed toward improved solubility, dissolution, oral pharmacokinetics and anticancer activity of the compound of formula A by use of different hydrophilic/amphiphilic/cross-linked polymers.

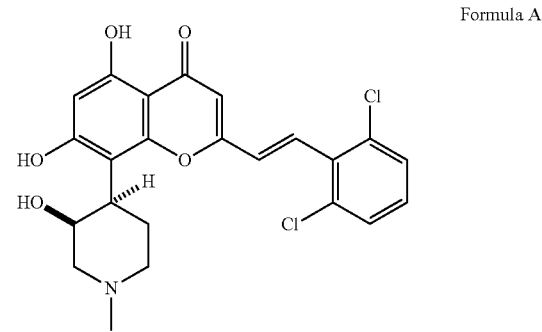 [SMILES: CN1CC[C@H](c2c(O)cc(O)c3c(=O)cc(/C=C/c4c(Cl)cccc4Cl)oc23)[C@H](O)C1]

Formula A

In-vivo PK and efficacy studies shows that the compound of formula A has a solubility/dissolution barrier. Various solubility enhancing approaches such as "Salt formation" though succeeded has not proved to be very beneficial. Whereas solid dispersion approach with hydrophilic polymers have shown surprising effect in removing the solubility/dissolution barrier. This invention for the first time discloses a dissolution-boosting formulation of the compound of formula A.

The solid dispersion according to one exemplary embodiment of present invention comprises a potent anticancer compound of "formula A" which displays anticancer effect by inhibiting various cyclin dependent kinases. The main targets of this compound are Cdk-2, 4, 6 and 9. The compound showed good anticancer activity both in in-vitro and in-vivo models. The compound showed in-vivo efficacy in pancreatic, colon and leukemia xenografts at 50 mg/kg, po. Various physicochemical properties including solubility and lypophilicity were determined and lypophilicity was found in average range (log P=3.10) but the water solubility of compound was low (10-20 µg/ml). The low water solubility was one of main reason for its in-vivo efficacy at higher dose (50 mg/kg). Therefore, the solid dispersions were prepared in order to enhance dissolution profile of the anticancer compound of formula A.

There is provided a novel drug delivery composition for the enhanced solubility and dissolution of this anticancer compound of Formula A, which in turn results in improved efficacy after oral administration. In particular, the solid dispersion increases the saturation solubility of anticancer compound in the GIT which results in higher absorption and in turn better oral bioavailability compared to its conventional doses form. These novel solid dispersions are comprised of various hydrophilic polymers alone or in combination.

The solid dispersion according to one exemplary embodiment of present invention is achieved by the use of pharmaceutical composition comprising the anticancer compound of formula A in combination with one or more hydrophilic polymers.

In accordance to the present invention, the preferred examples of hydrophilic polymer includes but not limited to hydroxypropylcellulose, hydroxypropylmethylcellulose, hydroxypropylmethylcellulose acetate succinate, polyvinylpyrrolidone K12-K120, polyvinyl alcohol, copolyvidone, polyethylene glycol, polyethylene glycol(15)-hydroxystearate, poly(ethylene glycol)-block-poly(propylene glycol)-block-poly(ethylene glycol), 2-hydroxypropyl-beta-cyclodextrin, etc.

In one preferred embodiment of the invention, the orally-administrable formulation for the improved dissolution profile of anticancer compound comprises uniformly dispersed anticancer compound in at least one hydrophilic polymer/excipient and is characterized by improved in-vitro dissolution profile of compound over a period of 6 hrs, as determined by U.S.P. dissolution apparatus by paddle method at a speed of 50 rpm and temperature 37° C.±0.5 under different dissolution sink conditions.

In one of the embodiment of the invention, at least 75% of the anticancer compound of Formula A is released within about 60 minutes in case of the solid dispersion, when tested in any dissolution test according to USP using an aqueous dissolution medium.

In one of the embodiment of the invention, a pharmaceutical composition comprises the solid dispersion of compound of formula A optionally with a pharmaceutically acceptable excipients.

In another preferred embodiment of the invention, the pharmaceutical composition is in the oral dosage form selected from the group consisting of a tablet or a hard gelatin capsule.

The invention also comprises a process for the preparation of an orally-administrable solid dispersion composition for the improved solubility and dissolution profile of the anticancer compound. The steps for the preparation of said composition comprising anticancer compound and PVP-K30 (povidone) are provided below. The solid dispersion formulations can be prepared by any method including solvent evaporation, fusion method, hot melt extrusion and supercritical fluid method. One exemplary formulation using solvent evaporation contains following steps:

a) making a solution of the anticancer compound in an organic solvent selected from the group consisting of methanol, ethanol, isopropyl alcohol, chloroform, dichloromethane, tetrahydrofuran and a combination thereof;
b) making a solution of the PVP-K30 in an organic solvent selected from the group consisting of methanol, ethanol, isopropyl alcohol, chloroform, dichloromethane, tetrahydrofuran and a combination thereof;
c) mixing the two solutions from step a & b in a desired ratio ranging from 1:1 to 1:10;
d) evaporating the solvent from the solution obtained in step c) using either vacuum drying or using spray dryer to obtain the dried product;
e) grinding of dried product obtained in step d) in moisture-free environment and passing through sieve #30 to obtain the solid dispersion;
f) preparing solid dispersion pharmaceutical composition in the form of tablet by pressing solid dispersion obtained in step (e) optionally with a pharmaceutical excipient or in the form of capsules by filling the solid dispersion in hard-gelatin capsules.

In another embodiment of the present invention, the solid dispersion of compound of formula A along with the compound of formula A was studied for comparative oral pharmacokinetics in rodent species.

In another embodiment of the present invention, the solid dispersion of compound of formula A along with the compound of formula A was tested for the in-vivo activity in Ehrlich Solid Tumor model.

Compound of formula A is an orally active potent anticancer compound and during formulation development of this compound, it was observed that it has low water solubility (10-20 µg/mL). This has resulted in its poor in-vitro dissolution profile of compound in different dissolution media. A water solubility of less than 100 µg/mL of any compound is considered as low at the discovery and developmental stages when the optimum dose of drug is not known.

This invention also provides the method for preparation of novel solid dispersion wherein the anticancer compound is dispersed in different hydrophilic/amphiphilic/cross-linked/biodegradable/non-biodegradable polymers using solvent evaporation (under vacuum/spray drying/lyophilization) method. The prepared solid dispersion is either formulated in a tablet or capsule using different pharmaceutical excipients.

Moreover, this invention provides dispersions wherein the water solubility and overall in-vitro dissolution profile of the compound are significantly improved. The water solubility of prepared solid dispersions along with compound of Formula A was determined using shake flask method, wherein the analysis was done by HPLC. The in-vitro dissolution studies were performed using U.S.P. type-2 (paddle type) dissolution apparatus at a speed of 50 rpm, and temperature of 37° C.±0.5, using 250 ml of dissolution media (0.25% SLS containing water and phosphate buffer pH 6.8 up to 6 h). Further, the solid dispersions were characterized using different analytical techniques such as DSC, FTIR, XRD, etc.

Novel oral solid dispersion containing anticancer compound of formula A was tested for in-vivo anticancer activity using Ehrlich Solid Tumor model. In this model, after oral administration of formulation VKB-SD75 and the compound of formula A in male Swiss mice up to 9 days, the % tumor growth inhibition was calculated on 13$^{th}$ day. Novel solid dispersion VKB-SD75 showed significantly improved anticancer activity compared to the compound of Formula A. The comparative in-vivo efficacy results are given in Table 3.

EXAMPLES

Following examples are given by way of illustration therefore should not be construed to limit the scope of the invention.

Example 1: Synthesis of Anticancer Compound of Formula A

Briefly, a 30 g of rohitukine (0.09834 moles) was dissolved in a solution of 500 ml methanol containing 38.5 g (0.69 moles, 7 equiv.) of KOH. To this mixture was added, 17.19 g (0.098 moles) of 2,6-dichlorobenzaldehyde and the resultant mixture was stirred at 100° C. for 3-4 hours. After completion of the reaction, the mixture was cooled and neutralized with 6 N HCl. The precipitate was filtered, and washed with 50 ml of methanol:water (30:70) to remove unreacted aldehyde and further washed with acetone. Finally, it was recrystallized using methanol:chloroform (20:80) to get compound of formula A in 62% yield (28 g).

Example 2: HPLC Method for Analysis of Compound of Formula A

For the analysis of compound of formula A, the reverse phase HPLC based method was developed. The HPLC analysis employed reversed-phase C18 Chromolith® performance RP-18e (100×4.6 mm, 5 micron, Merck) column using photodiode detector (SPD-M20A, Prominence, Shimadzu). Gradient elution (20 min.) with mobile phase A was methanol and B was 0.1% v/v formic acid in water. The gradient system comprises: 70% B for 0-2 min, 70-30% B from 2-10 min, 30% B from 10-12 min, 30-70% B from 12-17 min, 70% B from 17-20 min. The injection volume was 3.0 μL (SIL-20A HT Prominence auto-sampler) with the flow rate of 1.0 ml/min (pump, LC-6AD Shimadzu liquid chromatography). The column oven temperature was kept at 37° C. (column oven, CTO-10ASVP). As shown in FIG. 1, the retention time of compound of Formula A was 11.99 min and calibration curve was plotted in a range from 1-160 μg/ml.

Example 3: pH Dependent Stability of Compound of Formula A

The stability of compound was performed in pH 1.2 buffer, pH 4.0 buffer, phosphate buffer pH 6.8, phosphate buffered saline pH 7.4, SGF (pH 1.2), SIF (pH 6.8) and plasma upto 24 hrs. The % compound hydrolyzed or degraded was determined by HPLC analysis. Results of stability studies indicated that compound was stable at all the conditions tested (the % drug remaining was >95%).

Example 4: Preparation of Novel Solid Dispersion Formulations of Compound of Formula A Solid dispersions were formulated as different formulations containing anticancer compound (formula A) along with different polymers in different proportions as shown in Table 1 and 2. First the anticancer compound and various excipients/hydrophilic polymers were weighed accurately. Both the compound and polymers were dissolved in methanol. Those polymers which were insoluble in methanol were dissolved in water. In next step, the compound and polymeric solutions were mixed in different ratio and transferred to the different wells of 24 well plates followed by evaporation of solvent by shaking at 300 rpm and 50° C. and drying in desiccators. After complete drying, the water solubility of compound was determined by shake-flask method followed by RP-TIPLC analysis. All formulations were prepared in triplicate.

TABLE 1

Polymeric formulation and water solubility of binary solid dispersion formulations

| Sr. No. | Polymer/coformer | Formulation code | Compound: polymer ratio | Solubility in water (μg/ml) value ± STDEV | Solubility improvement in folds |
|---|---|---|---|---|---|
| 1 | Kolliphor HS 15 | VKB-SD1 | 1:2 | 46.17 ± 18.51 | 4 |
| 2 | (Polyethylene glycol (15)-hydroxystearate) | VKB-SD2 | 1:4 | 65.38 ± 24.76 | 7 |
| 3 | PEG-PPG-PEG | VKB-SD3 | 1:2 | 42.01 ± 4.17 | 4 |
| 4 | (PEG block polymer) | VKB-SD4 | 1:4 | 129.35 ± 11.61 | 14 |
| 5 | Synperonic F-108 | VKB-SD5 | 1:2 | 102.19 ± 17.56 | 11 |
| 6 | (PEG block polymer) | VKB-SD6 | 1:4 | 115.88 ± 6.57 | 12 |
| 7 | HP-β-CD | VKB-SD7 | 1:2 | 61.75 ± 7.74 | 6 |
| 8 | | VKB-SD8 | 1:4 | 55.08 ± 4.76 | 5 |
| 9 | PVP-K40 | VKB-SD9 | 1:2 | 79.50 ± 21.21 | 8 |
| 10 | | VKB-SD10 | 1:4 | 115.45 ± 8.02 | 12 |
| 11 | PVP-K1300 | VKB-SD11 | 1:2 | 65.95 ± 28.60 | 7 |
| 12 | | VKB-SD12 | 1:4 | 75.96 ± 27.40 | 8 |
| 13 | PVP-K30 | VKB-SD13 | 1:2 | 74.23 ± 26.95 | 8 |
| 14 | | VKB-SD14 | 1:4 | 159.14 ± 15.05 | 17 |
| 15 | PVP-K90 | VKB-SD15 | 1:2 | 65.68 ± 29.83 | 7 |
| 16 | | VKB-SD16 | 1:4 | 94.97 ± 20.51 | 10 |
| 17 | PEG 1500 | VKB-SD17 | 1:2 | 72.82 ± 4.63 | 7 |
| 18 | | VKB-SD18 | 1:4 | 84.48 ± 11.96 | 9 |
| 19 | PEG 4000 | VKB-SD19 | 1:2 | 26.49 ± 7.45 | 2 |
| 20 | | VKB-SD20 | 1:4 | 75.62 ± 13.58 | 8 |
| 21 | Poloxamer 188 | VKB-SD21 | 1:2 | 10.34 ± 1.53 | 0 |
| 22 | (PEG block polymer) | VKB-SD22 | 1:4 | 48.79 ± 17.57 | 5 |
| 23 | Methocel K15M | VKB-SD23 | 1:2 | 21.99 ± 5.82 | 2 |
| 24 | | VKB-SD24 | 1:4 | 15.90 ± 5.24 | 1 |
| 25 | Methocel K4M | VKB-SD25 | 1:2 | 24.70 ± 7.54 | 2 |
| 26 | | VKB-SD26 | 1:4 | 10.70 ± 2.38 | 0 |
| 27 | HPMC 5 cps | VKB-SD27 | 1:2 | 24.30 ± 2.15 | 2 |
| 28 | | VKB-SD28 | 1:4 | 14.13 ± 4.20 | 1 |
| 29 | HPMC 15 cps | VKB-SD29 | 1:2 | 33.99 ± 6.54 | 3 |
| 30 | | VKB-SD30 | 1:4 | 9.59 ± 0.40 | 0 |
| 31 | HPMC 50 LV | VKB-SD31 | 1:2 | 29.70 ± 6.91 | 2 |

TABLE 1-continued

Polymeric formulation and water solubility of binary solid dispersion formulations

| Sr. No. | Polymer/coformer | Formulation code | Compound: polymer ratio | Solubility in water (µg/ml) value ± STDEV | Solubility improvement in folds |
|---|---|---|---|---|---|
| 32 |  | VKB-SD32 | 1:4 | 7.62 ± 0.62 | 0 |
| 33 | PEG-PPG-PEG | VKB-SD37 | 1:6 | 114.83 ± 4.45 | 12 |
| 34 |  | VKB-SD38 | 1:8 | 123.54 ± 19.64 | 13 |
| 35 | PVP-K30 | VKB-SD39 | 1:6 | 98.77 ± 6.52 | 10 |
| 36 |  | VKB-SD40 | 1:8 | 188.53 ± 10.30 | 21 |
| 37 | PEG-4000 | VKB-SD41 | 1:6 | 66.09 ± 6.88 | 7 |
| 38 |  | VKB-SD42 | 1:8 | 82.53 ± 3.89 | 9 |
| 39 | PVP-K30 | VKB-SD75 | 1:4 | Scale up batch of VKB-SD14 | |

TABLE 2

Polymeric formulation and solubility of ternary solid dispersion formulations

| Sr. No. | Formulation code | Polymer/ coformer | Compound: polymer 1: polymer 2 ratio | Solubility in water (µg/ml) Value ± STDEV | Solubility improvement in folds |
|---|---|---|---|---|---|
| 1 | VKB-SD45 | PEG- | 1:1:1 | 59.32 ± 21.31 | 6 |
| 2 | VKB-SD46 | PPG- | 1:1:2 | 55.41 ± 15.59 | 5 |
| 3 | VKB-SD47 | PEG (1) | 1:1:4 | 81.92 ± 9.99 | 9 |
| 4 | VKB-SD48 | PVP- | 1:2:1 | 65.04 ± 9.86 | 7 |
| 5 | VKB-SD49 | K30 (2) | 1:2:2 | 27.46 ± 6.00 | 2 |
| 6 | VKB-SD50 |  | 1:2:4 | 55.83 ± 28.66 | 5 |
| 7 | VKB-SD51 |  | 1:4:1 | 98.77 ± 8.62 | 10 |
| 8 | VKB-SD52 |  | 1:4:2 | 94.59 ± 15.01 | 10 |
| 9 | VKB-SD53 |  | 1:4:4 | 125.50 ± 17.96 | 14 |

Example 5: Determination of Aqueous Solubility of Solid Dispersion Formulations and Compound of Formula A The water solubility of formulations prepared in Example 4 and compound of Formula A was determined in each well of plate containing different solid dispersion formulations. Briefly, for solubility determination the distilled water was added to each well and the plate was shaked at 25° C. for 24 hrs followed by transfer of supersaturated solution to eppendorf tube and centrifuged at 10,000 g for 10 min. The supernatant was then analyzed by RP-HPLC. The solubility results are shown in Table 1 and 2.

Example 6: Dissolution Profile of Solid Dispersion Formulations

The dissolution profile of compound and solid dispersion formulation VKB-SD75 was studied in sink conditions. For the sink condition, 0.25% SLS was added to dissolution media and dissolution was studied in water and pH 6.8 phosphate buffer (Ilevbare, G. A. et al., *Pharmaceutical amorphous solid dispersions*, Eds. John Wiley & Sons 2015, pp. 218). The dissolution studies were carried out using Lab-India Dissolution Tester (Model: DS 8000; apparatus 2—Paddle Apparatus) at 50 rpm and 37° C.±0.5 and dissolution media volume was 250 mL. Formulation equivalent to 10 mg of compound was added to each dissolution vessel in triplicate and 1 ml sample was taken and replaced by fresh dissolution media at different time points (0.25, 0.50, 1, 2, 4, 6 hrs).

Figure 2:
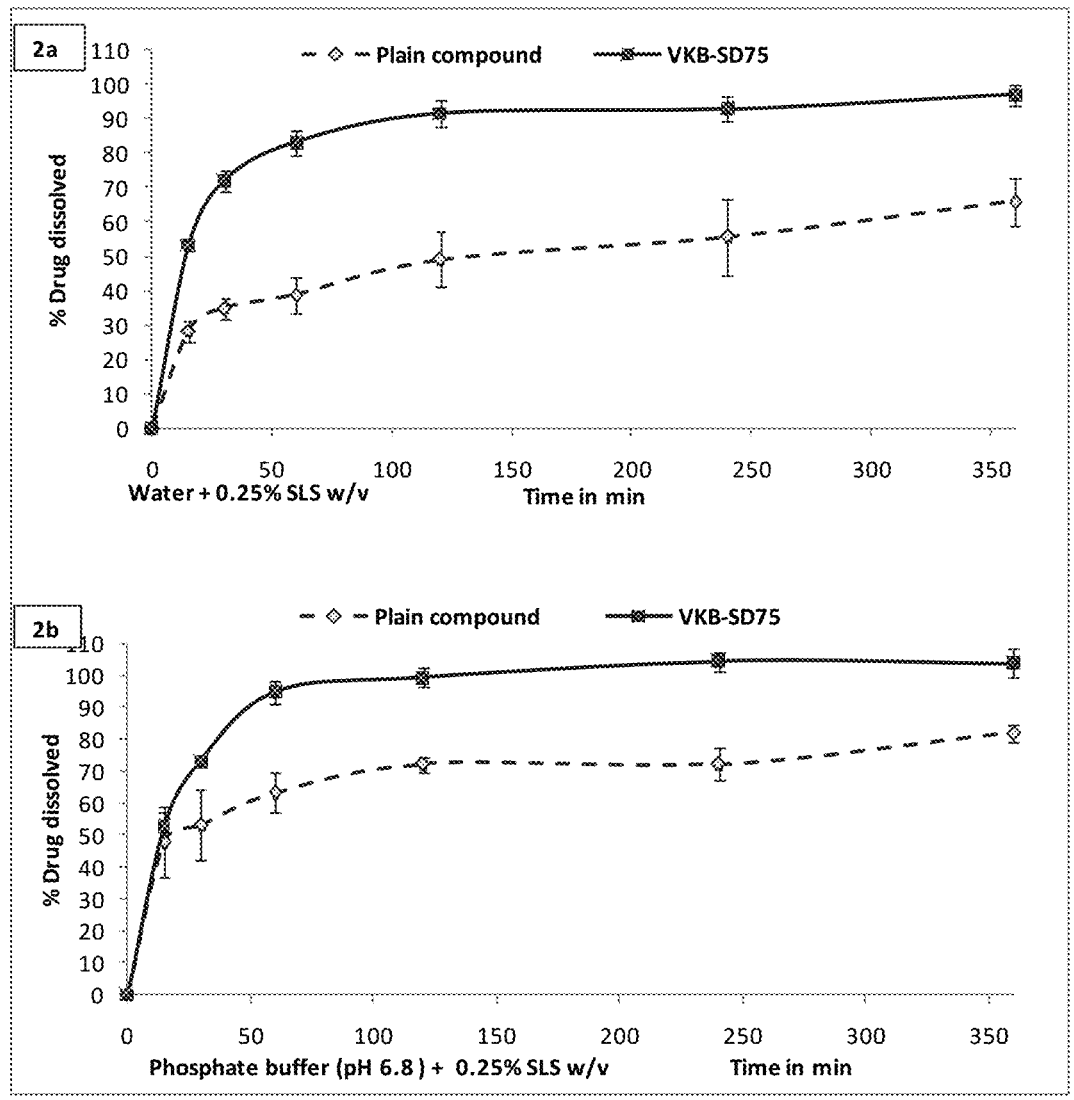
FIG. 2 shows the in-vitro dissolution profiles of developed solid dispersion formulations along with compound of Formula A in water (2A) and phosphate buffer pH 6.8 (2B). Both the dissolution media were containing 0.25% SLS for maintaining the sink condition.

The percentage drug dissolved was determined by HPLC analysis. Solid dispersion formulation showed higher dissolution compared to the compound of Formula A in water containing 0.25% SLS. After 2 h of dissolution as shown in FIG. 2A, solid dispersion formulation VKB-SD75 showed >90% drug dissolved which was significantly higher compared to compound of Formula A which showed only 49.15% drug dissolved at the same time. While in case of dissolution in phosphate buffer (pH 6.8, 0.25% SLS) (FIG. 2B), formulation VKB-SD75 showed enhanced dissolution compared to the compound of Formula A. Formulation VKB-SD75 showed 95% drug dissolution while the compound of Formula A showed only 63% dissolution after 1 h. After 6 h, the drug dissolution was higher in case of solid dispersion formulation compared to compound of Formula A. The dissolution profile of solid dispersion formulations are shown in FIG. 2A-B.

Figure 3:
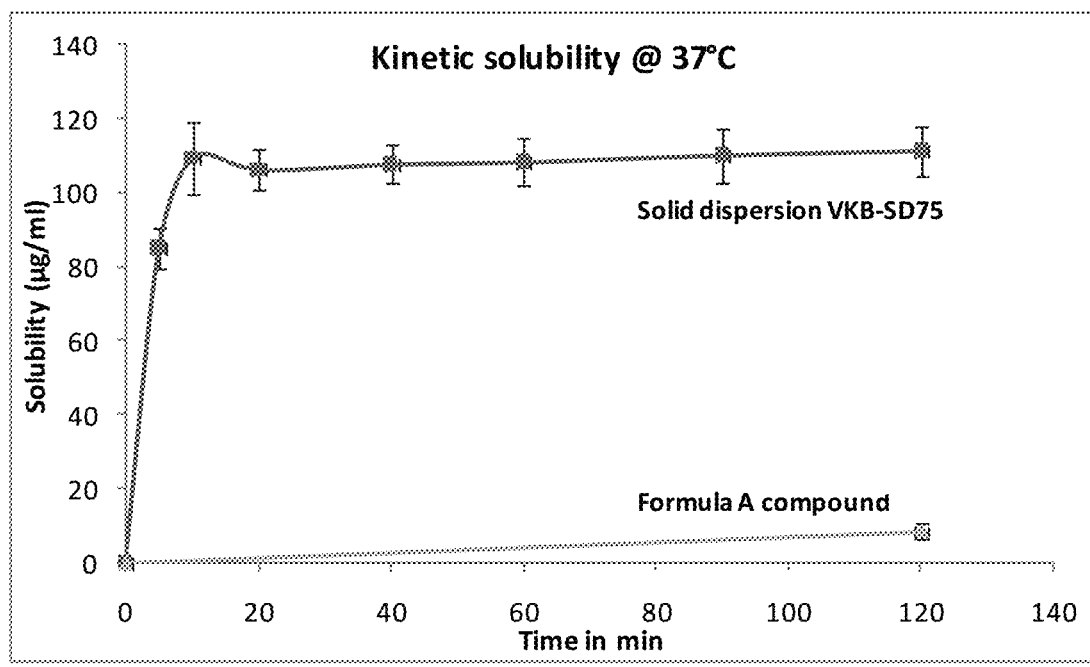
FIG. 3 shows the comparison between time-dependent solubility of compound of formula A and its solid dispersion formulation VKB-SD75.

Example 7: Characterization of Solid Dispersion Formulations Using FTIR, DSC and PXRD Solid dispersion formulations as prepared in Example 4 were characterized for polymer compatibility, interaction between polymer and compound and polymorphic form of compound in formulation i.e. amorphous or crystalline. Fourier-transform infrared spectroscopic (FTIR) and differential scanning calorimetric analysis showed the compatibility of polymers with the compound and indicates the presence of hydrogen bonding interactions were between the polymer and compound in all the three formulations. Powder X-ray diffraction (PXRD) analysis showed that, in formulation VKB-SD75, the compound was present in crystalline form and most of the X-ray diffraction peaks corresponding to compound were found present Example 8: Kinetic/Time Dependent Solubility Profile of Solid Dispersion Formulations Time dependent solubility profile of compound of Formula A and solid dispersion formulation VKB-SD75 were determined at 37° C. in distilled water over a period of 120 min. As shown in FIG. 3, the solid dispersion formulations showed a saturation solubility of >100 µg/ml which was significantly higher compared to the compound of Formula A (10-20 µg/ml). Further up to 120 minutes of study, same high concentration of compound was maintained in case of solid dispersion formulation which was ~10 fold higher compared to the compound of Formula A. The kinetic solubility profile of VKB-SD75 is shown in FIG. 3.

Figure 4:
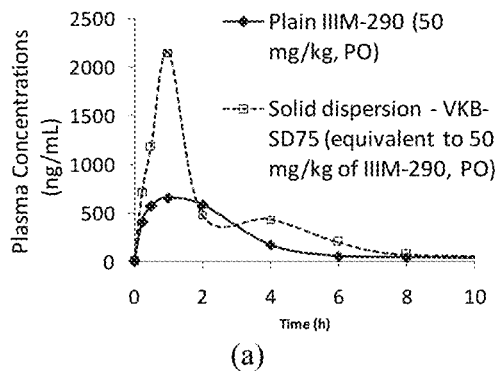
FIG. 4 shows the comparative oral pharmacokinetics of compound of formula A (herein referred as plain IIM 290) and its solid dispersion formulation VKB-SD75. (A) The time versus plasma concentration curve (B) pharmacokinetic parameters of "compound of formula A" and its solid dispersion formulation along with fold-increase values.

Example 9: The Comparative Oral Pharmacokinetic Study of Compound of Formula a Versus its Solid Dispersion Formulation VKB-SD75 in BALB/c Mice In the comparative oral pharmacokinetic study of compound of formula A versus its solid dispersion formulation "VKB-SD75", the dose of 50 mg/kg of compound of formula A was administered in BALB/c mice in both these groups. The vehicle used for PK study was 1% v/v Tween 80 in 0.5% sodium CMC in water. Blood samples were collected (n=3/time point) at 0.083 (IV only), 0.25, 0.5, 1, 2, 4, 8 and 24 h, post-dose. At each time point about 200 µL of blood was collected by jugular vein into a labeled microfuge tube containing 200 mM K$_2$EDTA solution (20 µL per mL of blood) and equivalent volume of heparinized saline was replaced following sample collection. The blood samples were processed to obtain the plasma samples within 30 min of scheduled sampling time. All plasma samples were stored below −60° C. until bioanalysis. The plasma samples were analyzed for compound of formula A content using a fit-for purpose LC-MS/MS method with a lower limit of quantification (LLOQ) of 5.05 ng/mL. The pharmacokinetic parameters of compound of formula A were calculated using the non-compartmental analysis tool of validated Phoenix® WinNonlin® software (version 6.3). Results are shown in FIG. 4A-B.

Following single oral gavage administration of compound of formula A (50 mg/kg) to male BALB/C mice, the mean time taken to reach peak plasma concentration ($T_{max}$) was found to be 1.00 h suggesting rapid rate of absorption. The exposure ($C_{max}$ and $AUC_{last}$) was found to be 656 ng/mL and 2570 ng·h/mL, respectively. Similarly, following single oral gavage administration of VKB-SD75 dose formulation in male BALB/C mice (50 mg/kg), the mean time to reach peak plasma concentration ($T_{max}$) of formula A compound was found to be 1.00 h. The exposure ($C_{max}$ and $AUC_{last}$) was found to be 2150 ng/mL and 4870 ng·h/mL, respectively. This results indicated that the solid dispersion formulation has resulted in 3.27 and 1.90-times improvement in the $C_{max}$ and $AUC_{last}$ of anticancer compound in comparison to the compound of Formula A.

Example 10: The Comparative In-Vivo Efficacy of Compound of Formula a and its Solid Dispersion VKB-SD75 in Murine Solid Tumor Model The in-vivo efficacy testing of best identified solid dispersion formulation VKB-SD75 was done using Ehrlich solid tumor model, parallelly with the compound of Formula A. Ehrlich Ascites Carcinoma (EAC) cells were collected from the peritoneal cavity of the Swiss mice weighing 18-23 g, harboring 8-10 days old ascetic tumor. 1×10$^7$ EAC cells were injected intramuscularly in the right thigh of Swiss male mice selected for the experiment on day 0. The next day, animals were randomized and divided into 8 groups. Seven treatment groups contained 7 animals each and one control groups contained 10 animals each. Treatment group 1-6 were treated with the compound of formula A and solid dispersion formulation at different dose strength once daily from day 1-9. The seventh treatment group was treated with 5-fluorouracil (22 mg/kg, i.p.) from day 1-9 and it served as positive control. The control group was similarly administered normal saline (0.2 ml, i.p) from day 1-9. On day 9 & 13, tumor-bearing thigh of each animal was shaved, and longest and shortest diameters of the tumor were measured with the help of vernier caliper. The percent tumor growth inhibition was calculated on day 13 by comparing the average values of treated groups with that of the control group. Tumor growth in saline-treated control animals was taken to be 100%.

Table 3 shows the % tumor growth inhibition results which showed that novel solid dispersion formulation significantly improved the oral efficacy of anticancer compound of formula A. Solid dispersion formulation VKB-SD75 showed 37.64% and 43.15% tumor growth inhibition at 50 and 75 mg/kg dose while the compound of Formula A showed 24.75% and 30.92% tumor growth inhibition at equivalent dose, without causing any mortality.

The effect of the compound of Formula A, which was observed at 100 mg/kg dose was obtained by the new formulation VKB-D75 at only the half-dose (50 mg/kg), as depicted in Table 3 (entry sr no 3 versus 5). Similarly, the compound of Formula A showed 30 TGI at 75 mg/kg, whereas similar TGI was observed with only 25 mg/kg dose of the new formulation VKB-SD75 (compare entry sr no 2 versus 4). These results clearly indicated the significant improvement in in-vivo efficacy of the anticancer compound, in the form of solid dispersion formulation.

TABLE 3

In-vivo tumor growth inhibition by compound of formula A and its solid dispersion formulation VKB-SD75 in Ehrlich Ascites Carcinoma solid tumor model.

| Sr. No. | Treatment group | % Tumor growth inhibition on 13th day | Mortality |
|---|---|---|---|
| 1 | Compound of formula A (50 mg/kg p.o) | 24.75 ± 3.52 | 0/7 |
| 2 | Compound of formula A (75 mg/kg p.o.) | 30.92 ± 5.32 | 0/7 |
| 3 | Compound of formula A (100 mg/kg p.o.) | 38.63 ± 3.65 | 0/7 |
| 4 | Solid dispersion VKB-SD75 (25 mg/kg p.o.) | 30.71 ± 5.64 | 0/7 |
| 5 | Solid dispersion VKB-SD75 (50 mg/kg p.o.) | 37.64 ± 4.64** | 0/7 |
| 6 | Solid dispersion VKB-SD75 (75 mg/kg p.o.) | 43.15 ± 2.63*** | 0/7 |
| 7 | Positive control-5-FU (22 mg/kg, i/p) | 49.44 ± 6.32 | 0/7 |
| 8 | Normal control-Normal saline (0.2 mL i/p) | — | 0/10 |

Statistical analysis was performed by comparing the treatment groups with plain compound at same dose [i.e. Sr no 1 versus 5; and Sr no 2 versus 6]. ns, P>0.05; , P<0.01; *P<0.001.

Example 11: Tablet Dosage Form of VKB-SD75 Solid Dispersion

The solid dispersion VKB-SD75 was compressed directly as a tablet along with filler (microcrystalline cellulose) and lubricant (sodium lauryl sulphate) using Tablet Punching Machine (Single Punch). The composition of the tablet is:
Solid dispersion VKB-SD75: 500 mg
Microcrystalline cellulose: 90 mg
Sodium lauryl sulphate: 10 mg Advantages of the Invention The main advantages of the present invention are:
1. The novel formulations provide higher dissolution of an anticancer compound in comparison to the compound of Formula A.
2. The novel formulations provide improved in-vivo efficacy in animal models of cancer.
3. The novel formulation has resulted in the reduction of the dose of compound up to 50%.
4. The solid dispersion formulation has better oral pharmacokinetic profile over the compound of Formula A.

The invention claimed is:

1. A solid dispersion comprising an anticancer compound (1'R,2'S)-2-(2,6-dichlorostyryl)-5,7-dihydroxy-8-(3-hydroxy-1-methylpiperidin-4-yl)-4H-chromen-4-one of Formula A dispersed in a hydrophilic polymer at an ambient temperature,

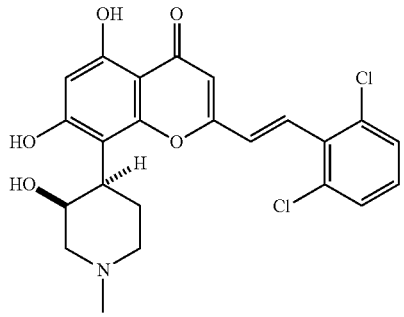

Formula A wherein the anticancer compound is present in a concentration range of 15% w/w to 30% w/w.

2. The solid dispersion as claimed in claim 1, wherein the hydrophilic polymer is selected from the group consisting of hydroxypropylcellulose, hydroxypropylmethylcellulose, hydroxypropylmethylcellulose acetate succinate, polyvinylpyrrolidone K12-K120, polyvinyl alcohol, copolyvidone, polyethylene glycol, polyethylene glycol(15)-hydroxystearate, poly(ethylene glycol)-block-poly(propylene glycol)-block-poly(ethylene glycol), 2-hydroxypropyl-beta-cyclodextrin and a combination thereof.

3. The solid dispersion as claimed in claim 1, wherein of the anticancer compound and the hydrophilic polymer(s) are in a weight ratio of 1:4.

4. The solid dispersion as claimed in claim 1, wherein at least 75% of the anticancer compound is released within about 60 minutes, when tested in a dissolution test using an aqueous dissolution medium according to USP.

5. The solid dispersion as claimed in claim 1, wherein the solid dispersion is configured to enhance plasma exposure and percent tumor growth inhibition by at least 1.5 times in comparison to the compound of formula A.

6. A pharmaceutical composition comprising the solid dispersion as claimed in claim 1 and a pharmaceutically acceptable excipients.

7. The pharmaceutical composition as claimed in claim 6, wherein the pharmaceutically acceptable excipients are selected from the group consisting of fillers, disintegrants, binders and lubricants.

8. The pharmaceutical composition as claimed in claim 7, wherein the fillers are selected from the group consisting of microcrystalline cellulose, dicalcium phosphate, sucrose, and lactose.

9. The pharmaceutical composition as claimed in claim 7, wherein the lubricants are selected from the group consisting of sodium lauryl sulphate, silicon dioxide, magnesium stearate, sodium benzoate, sodium acetate, sodium carboxymethyl cellulose, and boric acid.

10. The pharmaceutical composition as claimed in claim 6, wherein the pharmaceutical composition is in a solid oral dosage form.

11. A method for the preparation of the solid dispersion as claimed in claim 1, the method comprising the step of dispersing the anticancer compound of formula A in a hydrophilic polymer to obtain a solid dispersion at ambient temperature, wherein the anticancer compound is present at a concentration of 15% w/w to 30% w/w.

12. The pharmaceutical composition as claimed in claim 6, wherein the pharmaceutical composition is configured to treat cancer.

* * * * *